United States Patent [19]

Lai

[11] 4,246,412
[45] Jan. 20, 1981

[54] SYNTHESIS OF 2-KETO-1,4-DIAZACYCLOALKANES WITH A SOFT ION CATALYST

[75] Inventor: John T. Lai, Broadview Heights, Ohio

[73] Assignee: The B. F. Goodrich Company, Akron, Ohio

[21] Appl. No.: 69,679

[22] Filed: Aug. 27, 1979

[51] Int. Cl.$^3$ .................. C07D 241/08; C07D 243/08
[52] U.S. Cl. .............................. 544/384; 260/239.3 R; 260/239.3 B
[58] Field of Search ................. 544/384; 260/239.3 R, 260/239.3 B

[56] References Cited

U.S. PATENT DOCUMENTS

| | | | |
|---|---|---|---|
| 4,167,512 | 9/1979 | Lai | 544/384 |
| 4,190,571 | 2/1980 | Lai et al. | 260/45.8 N |

*Primary Examiner*—Jose Tovar
*Attorney, Agent, or Firm*—J. Hughes Powell, Jr.; Alfred D. Lobo

[57] ABSTRACT

A phase transfer catalyzed "soft ion synthesis" is disclosed in which the presence of a "soft ion" generated in situ by a soft ion catalyst has a directive effect which favors the formation of a polysubstituted 2-keto-1,4-diazacycloalkane isomer having substituents on both $N^4$-adjacent carbon atoms ("C atoms") of its diaza ring; this isomer is formed at the expense of isomers in which an $N^4$-adjacent C atom is not substituted. Such an isomer which has substituents on each $N^4$-adjacent C atom is generally more effective as a u-v light stabilizer than an isomer which has an unsubstituted $N^4$-adjacent C atom, and therefore the former is more desirable.

A liquid phase reaction of an acyclic 1,2-diamine with a monoketone or monoaldehyde in the presence of a phase transfer catalyst, a haloform and alkali is disclosed, in which reaction a soft ion catalyst which generates a soft ion selected from the group consisting of cyanide, iodide and thiocyanate, has a directive effect on the reaction so as to produce more isomer with substituents on each $N^4$-adjacent C atom than would be formed, under identical conditions but without the presence of the soft ion. The directive effect of the soft ion appears to enhance any directive effect that a particular phase transfer catalyst may exhibit.

8 Claims, No Drawings

SYNTHESIS OF 2-KETO-1,4-DIAZACYCLOALKANES WITH A SOFT ION CATALYST

BACKGROUND OF THE INVENTION

Organic materials, whether natural or synthetic, are conventionally protected against degradation by ultraviolet (UV) light by incorporating a UV light stabilizer in the materials. Many classes of compounds are known to be useful UV light stabilizers, some being more effective than others. Particularly effective compounds, which provide compositions resistant to degradation by UV light, include the 2-keto-1,4-diazacycloalkanes disclosed in my copending U.S. patent application Ser. No. 835,065 to be issued as U.S. Pat. No. 4,190,571.

Several syntheses of 2-keto-1,4-diazacycloalkanes with various substituents on the diaza ring are disclosed in my copending U.S. patent application Ser. No. 916,640 now issued as U.S. Pat. No. 4,167,512. In one synthesis (referred to as "the cyanohydrin synthesis") a cyclic or acyclic 1,2-diamine is reacted with an acyclic or cyclic cyanohydrin in the presence of a suitable organic solvent, and in the presence of solid or aqueous NaOH at ambient temperature and pressure, in the presence of an onium salt phase transfer catalyst in conjunction with a haloform.

In my copending patent application Ser. No. 057,238, and in said U.S. Pat. No. 4,167,512, a synthesis (referred to as "the ketoform synthesis") is disclosed in which a preselected 1,2-diamine is reacted with a saturated acyclic or cyclic monoketone, and, a haloform, in the presence of (i) a phase transfer catalyst (ii) an organic solvent, and (iii) solid or aqueous alkali. The phase transfer catalyst is selected from the group consisting of a tertiary or quaternary compound of an element selected from Groups VA and VIA of the Periodic Table, and, a polyether. Polyether phase transfer catalysts are especially noteworthy for their highly directive effect, that is, their ability to direct substituents on to the $N^4$-adjacent C atoms which are the more desirable positions of a diaza ring, so that polysubstituted compounds so formed exhibit exceptional UV light stability. The "soft ion synthesis" of this invention, in which, as in the ketoform synthesis, the presence of a monoketone or monoaldehyde is essential, a "soft ion", described hereinbelow, further enhances the directivity of the ketoform synthesis.

The substituted 2-keto-1,4-diazacycloalkanes with dialkyl substituents on each of two $N^4$-adjacent carbon ("C") atoms (also referred to as "symmetrical C atoms") are particularly effective u-v light stabilizers, having been generally found to be more effective than isomers in which the same substituents are otherwise substituted, that is, one $N^4$-adjacent atom of the isomer's diaza ring is unsubstituted. Though all isomers having plural substituents on the diaza ring are referred to herein as being polysubstituted, the more desirable isomers have substituents on each $N^4$-adjacent C atom of the diaza ring. The less desirable (because they are less effective as u-v stabilizers) isomers have an unsubstituted $N^4$-adjacent C atom. This invention is directed to a synthesis in which a "soft ion" catalyst is used to produce a directive effect; and thus favorably direct or bias the formation of the more desirable isomer at the expense of the less desirable one.

SUMMARY OF THE INVENTION

It has been discovered that a polysubstituted 2-keto-1,4-diazacycloalkane compound, having substituents on both $N^4$-adjacent C atoms of the diaza ring, is preferentially formed when a phase transfer catalyzed reaction which produces the compound is additionally catalyzed with a "soft ion" catalyst. By "soft ion" I refer to an anion with a large atomic radius, a low effective nuclear charge, low electronegatively, high polarizability, and easy oxidizability or empty low lying levels, as more fully described in "Hard and Soft Acids and Bases Principle in Organic Chemistry" by T. L. Ho, Academic Press, New York, N.Y. 1977. Isomers having substituents on each of the $N^4$-adjacent C atoms of the diaza ring are more effective u-v light stabilizers than those which have an unsubstituted symmetrical C atom, and the former are therefore more desirable.

It is therefore an object of this invention to provide a phase transfer catalyzed process in which a "soft ion" is used to favor, or bias due to its directive effect, the formation of isomers of polysubstituted 2-keto-1,4-diazacycloalkanes which have substituents on symmetrical C atoms of the diaza ring.

More specifically, it has been discovered that a more desirable isomer having substituents on $N^4$-adjacent C atoms, is preferentially formed by reacting in liquid phase (A) an acyclic 1,2-diamine with (B) a compound having a carbonyl bond selected from the group consisting of monoketones and monoaldehydes, in the presence of (i) a soft ion generated in situ, and also, (ii) a haloform, (iii) alkali, and (iv) a phase transfer catalyst selected from the group consisting of tertiary and quaternary compounds of Group VA and Group VIA elements, said soft ion and said phase transfer catalyst being together present in an amount sufficient to form said polysubstituted 2-keto-1,4-diazacycloalkane in a ratio of at least 5 parts by weight of more desirable isomer to 1 part of less desirable isomers. Specific soft ions which exhibit desirable directivity are cyanide, iodide and thiocyanate.

DETAILED DESCRIPTION OF PREFERRED EMBODIMENTS

The basic structure of the compounds prepared by the synthesis described herein, is a polysubstituted (hereafter also referred to as "substituted" for brevity) 2-keto-1,4-diazacycloalkane having (a) a fixed two-carbon bridge between the two N atoms (the $N^1$ and $N^4$ atoms) of the diaza ring, the remaining portion of the ring having a variable length bridge of two or more carbon atoms, (b) an $N^1$-adjacent carbonyl in the fixed two-carbon bridge, and (c) at least the $N^4$-adjacent C atom of the fixed two-carbon bridge has two substituents (hence "polysubstituted"), which may be cyclizable, that is, form a cyclic substituent. These polysubstituted compounds may be (a) monocyclic with a total of at least three acyclic substituents, at least two of which are on the $N^4$-adjacent C atom of the fixed two-carbon bridge; or, (b) polycyclic, with cyclizable substituents which may be cyclized into one, two or more unfused (spiro) rings; and, (c) the polysubstituted compounds may form dimers and bis-compounds.

The diaza ring of the compounds' basic structure may have from 6 to 9 ring members, and more preferably from 6 to 8 ring members. Most preferably the diaza ring of the basic structure has 6 or 7 ring members, that is, the compounds are either substituted piperazin- 2-ones, or, 1,4-diaza-2-keto-cycloheptanes (also termed "2-keto-diazepines"), or, dimers or bis-compounds thereof. Typically these substituted 2-keto-1,4-diazacycloalkanes preferably have two substituents, which may be cyclizable, on the $N^4$-adjacent C atom of the fixed two-carbon bridge, and at least one substituent on the other $N^4$-adjacent C atom. Most preferred are those substituted compounds which have two substituents, which may be cyclizable, on each $N^4$-adjacent C atom of the diaza ring (hence "tetra-substituted"). Among the isomers of tetra-substituted compounds, those in which the substituents are present on $N^4$-adjacent C atoms are more desirable, because they are more effective u-v light stabilizers, than isomers having an unsubstituted $N^4$-adjacent C atom.

As stabilizers, the foregoing compounds are used in the range from about 0.01 to about 5 parts by weight, and preferably from about 0.1 to about 1.0 part per one hundred parts (phr) of organic material subject to UV light. These materials may be low or high molecular weight materials, and particularly include homopolymers, copolymers and mixtures thereof. Examples of materials that can be stabilized against degradation due to UV light are oils; monomers, particularly $\alpha,\beta$-olefinically unsaturated monomers such as acrylates, dienes, vinyl nitriles, and the like; and other relatively lower molecular weight materials than synthetic resinous polymers, such as alcohols, aldehydes, and the like. Examples of known materials which can be stabilized with polysubstituted 2-keto-1,4-diazacycloalkanes are natural rubber, synthetic rubbers such as cis-polyisoprene, styrene-butadiene rubber, diene-nitrile rubbers, polyepihalohydrin polymers, polyurethanes, PVC resins, ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethyl-vinyl acetate polymers, and the like. The substituted 2-keto-1,4-diazacycloalkanes can also be used to stabilize mixtures and blends of polymeric materials such as ABS resin blends, PVC and polymethacrylate blends, and blends of polyolefin homopolymers and copolymers such as blends of polypropylene in epdm polymers.

The 2-keto-1,4-diazacycloalkanes prepared by the synthesis of this invention have the structural formula:

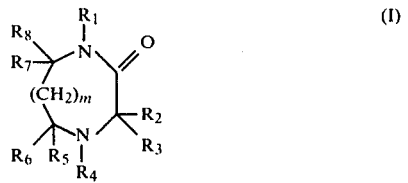
(I)

wherein, m represents an integer in the range from 0 to 2, being the number of additional methylene groups forming a bridge of variable length, and some of which groups may be substituted; when m is 0 then (I) represents a substituted 2-keto-piperazine, and when m is 1, then (I) represents a substituted 2-keto-diazepin;

$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether groups having from 3 to about 18 carbon atoms, hydroxyalkyl ether or cyanoalkyl ether groups having from 4 to about 18 carbon atoms, alkenyl or aralkyl having from 7 to about 14 carbon atoms, alkylene having from 2 to about 7 carbon atoms and optionally containing a phosphite, ester or hindered phenol group;

$R_4$ may be oxygen;

$R_2$, $R_3$, $R_5$, $R_6$, $R_7$ and $R_8$ independently each represent alkyl having from 1 to about 12 carbon atoms, haloalkyl having from 1 to about 12 carbon atoms, cyanoalkyl having from 2 to about 12 carbon atoms, aminoalkyl or iminoalkyl having from 2 to about 12 carbon atoms, cycloalkyl having from 5 to about 14 carbon atoms, hydroxy-cycloalkyl having from 5 to about 14 carbon atoms, alkenyl and aralkyl having from 7 to about 14 carbon atoms, alkylene having from 2 to about 7 carbon atoms and optionally containing a phosphite, ether or hindered phenol group, and which in combination, one with another, represent cycloalkyl having from 5 to about 14 carbon atoms at least four of which are cyclized and optionally containing a keto, ester, amide, ether, thio or hydroxy group;

$R_7$ and $R_8$ in addition may each independently represent hydrogen, and, either $R_5$ or $R_6$ may be hydrogen when the other is not.

The more desirable and more effective isomers (based on the presence of a comparable weight percent of stabilizer in stabilized organic material) preferentially formed by the soft ion catalytic synthesis of this invention are represented by a structural formula selected from

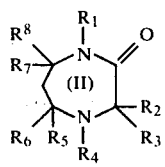 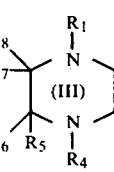 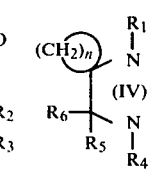 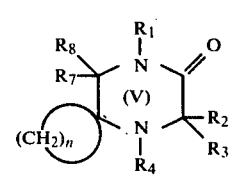

wherein n represents an integer in the range from 0 to about 6; so when n=0, then (IV) and (V) represent substituted 2-keto-piperazines; and when n=5, then (IV) and (V) represent 2-keto-piperazines with a 5,5-pentamethylene substituent; and, all the substituents have the same connotation as that set forth hereinabove.

The less desirable isomers formed, if at all, by the soft ion catalytic synthesis of this invention are represented by a structural formula selected from

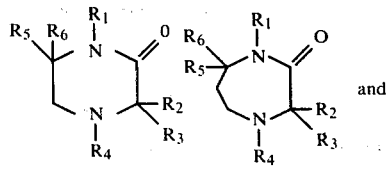

and

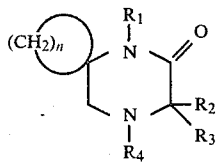

wherein all the substituents have the same connotation as that set forth hereinabove.

Illustrative of the type of substituents that provide effective stabilization in the above-identified 2-keto-diazacycloalkanes are:

where $R_1$ and/or $R_4$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R_1$ and/or $R_4$ is hydroxyalkyl, examples are 2-hydroxyethyl, 2-hydroxypropyl, 3-hydroxypropyl, 2-hydroxybutyl, 6-hydroxyhexyl, 8-hydroxyoctyl, and the like;

where $R_1$ and/or $R_4$ is haloalkyl, examples are 2-chloroethyl, 2-bromoethyl, 2-fluoroethyl, 2-chlorobutyl, 4-chlorobutyl, 2-chloroethylhexyl, and the like;

where $R_1$ and/or $R_4$ is cyanoalkyl, examples are 2-cyanoethyl, 3-cyanopropyl, 4-cyanobutyl, 8-cyanooctyl, and the like;

where $R_1$ and $R_4$ is aminoalkyl or iminoalkyl, examples are 2-aminoethyl, 3-aminopropyl, 4-aminobutyl, 6-aminohexyl, 2-methyl-2-aminoethyl, and the like;

where $R_1$ and $R_4$ is ether, examples are methoxyethyl, ethoxyethyl, ethoxypropyl, octyloxyethyl, phenoxyethyl, p-methylphenoxypropyl, and the like; when $R_1$ and/or $R_4$ is hydroxyalkylether or cyanoalkyl ether, examples are 2-hydroxyethyloxaethyl, p-(2-hydroxypropyl)-phenyloxapropyl, 4-hydroxybutyloxahexyl, 2-cyanoethyloxaethyl, 2-hydroxyethyl-di(oxaethyl), and the like;

for $R_2$, $R_3$, $R_5$, $R_6$, $R_7$, and $R_8$, examples are methyl, ethyl, propyl, n-butyl, isobutyl, n-hexyl, 2-ethylheptyl, n-decyl, and where the substituents are cyclizable, cyclopentyl, methylcyclopentyl, cyclohexyl, methylcyclonexyl, dimethyl cycloheptyl, piperidyl, 2-2',6-6'-tetramethyl piperidyl, and the like.

The more preferred substituted 2-keto-1,4-diazacycloalkane compounds are those wherein: $R_1$ and/or $R_4$ is selected from the group consisting of alkyl having from 4 to 18 carbon atoms, benzyl, cyclohexylmethyl, hydroxyalkyl having from 1 to about 6 carbon atoms, hydroxyalkyl ether having from 4 to about 12 carbon atoms, cyanoalkyl having from 2 to about 6 carbon atoms, and aminoalkyl having from 1 to about 6 carbon atoms, $R_2$, $R_3$, $R_5$ and $R_6$ are selected from the group consisting of alkyl having from 1 to about 12 carbon atoms, and polymethylene having from 5 to 6 carbon atoms which are cyclizable; only $R_2$, $R_3$ may be cyclized, or $R_2$, $R_3$ and $R_5$, $R_6$ may be cyclized; and, n is a numeral in the range from 4 to about 6 when the methylene groups are cyclized.

Examples of the aforespecified more preferred substituted monoketo-diazaalkan-2-ones are:

$N^4$-($\beta$-hydroxyethyl)-3,3,6-trimethyl-piperazin-2-one;

$N^4$-($\beta$-hydroxyethyl)3,3-pentamethylene-5,5-dimethyl-piperazin-2-one;

$N^4$-($\beta$-hydroxyethyl)3,3,6-trimethyl-diazepin-2-one;

$N^4$-($\beta$-hydroxyethyl)3,3,6,6-tetramethyl-diazepin-2-one;

$N^4$-($\beta$-hydroxyethyl)3,3-pentamethylene-5,5-hexamethylene-diazepin-2-one;

$N^4$-($\beta$-hydroxyethyl)3,3-pentamethylene-diazepin-2-one;

$N^4$-($\beta$-hydroxyethyl)3,3,5,5,7,7-hexamethyl-diazepin-2-one;

$N^4$-($\beta$-hydroxyethyl)3,3-pentamethylene-5,5,7,7-tetramethyl-diazepin-2-one;

$N^4$-($\beta$-hydroxyethyl)3,3-dimethyl-5,5-pentamethylene-piperazin-2-one;

$N^4$-($\beta$-hydroxyethyl)3,3,6,6-tetraethyl-5,5-pentamethylene-diazepin-2-one; and, $N^4$-($\beta$-hydroxyethyl)3,3-dimethyl-5,6-tetramethylene-diazepine-2-one.

Most preferred substituted mono-keto-1,4-diazaalkan-2-ones are:

$N^1$-dodecyl-3,3,5,5-tetramethyl-2-piperazinone;

$N^1$-t-octyl-3,3,5,5-tetramethyl-2-piperazinone;

1,2-ethane-bis-(N'-3,3,5,5-tetramethyl-2-piperazinone;

$N^4$-t-octyl-3,3,6,6-tetramethyl-2-piperazinone;

$N^1$-phenyl-3,3,5,5-tetramethyl-2-piperazinone;

$N^1$-t-butyl-3,3-dimethyl-5,5-pentamethylene-2-piperazinone; and, $N^1$-butyl-3,3,5,5,7-pentamethyl-1,4-diazepin-2-one.

It will now be evident that many of the substituents identified hereinabove may not be made directly by the syntheses of this invention, but by additional steps after having formed the substituted 2-keto-1,4-diazacycloalkane. These additional steps are well known to those skilled in the art, and do not require detailed description herein. In particular, dimers and bis compounds of substituted 2-keto-1,4-diazacycloalkanes can be prepared by knowm methods, once the desired 2-keto-1,4-diazacycloalkane is obtained by a chosen synthesis.

The "soft ion" catalytic synthesis of this invention is found to favor formation of the more desirable isomer when 1,2-diamines are reacted with a saturated or unsaturated monoketone or monoaldehyde and a haloform reactant, in an organic solvent for the reactants, in the presence of aqueous or solid alkali, provided there is also supplied a phase transfer catalyst consisting of "an onium salt" including a quaternary or tertiary organic compound of a Group VA or VIA element of the Periodic Table, and salts thereof. More preferred are the tertiary amines, quaternary amines, and salts thereof. The reaction may be carried out at any temperature within a wide range from about the freezing point of the reaction mass to about the reflux temperature of the solvent, provided it is lower than a temperature which is deleterious to the 2-keto-1,4-diazacycloalkane formed. The reaction is of particular interest because it generally proceeds at a temperature in the range from about $-20°$ C. to about room temperature (about 25° C.), with satisfactory speed, and with excellent yield of the more desirable isomer. The reaction may also be carried out at lower or higher temperatures and corresponding pressure from subatmospheric to superatmospheric, but atmospheric pressure is preferably employed for convenience, and because there appears to be no substantial advantage to be gained from operating at higher pressures.

The 1,2-diamines may include two primary amine moieties, one primary amine moiety and one secondary amine moiety, or two secondary amine moieties. The amine is chosen to provide, upon cyclization, the desired number of C atoms in the variable length bridge, and also to provide the desired substituents on preselected C atoms of this bridge. Among such desired substituents may be cyclic substituents, particularly cycloalkyl having from 5 to about 14 carbon atoms at least four of which are cyclized, and optionally containing a keto, ester, amide, ether, thio or hydroxy group. It will thus be evident that a straight chain or acyclic diamine, with desired substituents whether cyclic or acyclic, will be appropriate where a monocyclo-1,4-diazacycloalkane is to be synthesized.

In general, any "soft ion" generated in situ by any soft ion catalyst may exhibit some directive effect. Preferred soft ion catalysts are acyclic and cyclic cyanohydrins such as acetone cyanohydrin and cyclohexanone cyanohydrin, inorganic cyanides, iodides and thiocyanates which are capable of generating cyanide, iodide and thiocyanate ions in situ, such as for example, ammonium cyanide, the alkali metal cyanides, the alkaline earth metal cyanides, ammonium iodide, the alkali metal iodides, the alkaline earth metal iodides, and the like. By alkali metals I refer particularly to lithium sodium and potassium, and by alkaline earth metals I refer particularly to calcium barium and strontium.

The amount of soft ion catalyst used is not critical, and in general, only a sufficient amount is used to produce the desired directivity, that is, a desirable ratio of an isomer with substituents on the $N^4$-adjacent C atoms of the diaza ring to the isomers having an unsubstituted $N^4$-adjacent C atom. As little as 0.01 equivalents of the soft ion catalyst is found to produce substantial directivity, though typically, from about 0.05 to about 0.3 equivalents are used. Larger amounts, up to about 0.5 equivalents or more may be used without adverse side effects, but there is no advantage to doing so, particularly since the excess catalyst must be separated from the desired isomer. Most preferred is a range from about 0.1 to about 0.3 equivalents, the precise amount chosen depending upon the characteristics of the particular reaction to be catalyzed.

By "onium salts" I more particularly refer to tertiary or quaternary amines and salts such as are generally used in the phase transfer catalysis of heterogeneous reactions in immiscible liquids. The general requirement for the onium salt chosen is that it be soluble in both the organic and aqueous phases, when these two liquid phases are present, and usually a little more soluble in the organic phase than the aqueous phase. The reaction will also proceed with a phase transfer catalyst when there is only a single organic liquid phase present, but such a reaction is less preferable than one in which both aqueous and organic liquid phases are present. A wide variety of onium salts is effective in this soft ion catalyzed synthesis.

The onium salts include the well-known salts, tertiary amines and quaternary compounds of Group VA elements of the Periodic Table, and some Group VIA elements such as are disclosed in U.S. Pat. No. 3,992,432 and in a review in Angewandte Chemie, International Edition in English, 16 493-558 (August 1977). Discussed therein are various anion transfer reactions where the phase transfer catalyst exchanges its original ion for other ions in the aqueous phase, making it possible to carry out chemistry there with the transportesd anion, including $OH^-$ ions.

The onium salts used in this synthesis include one or more groups having the formula $(R_nY)^+X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+X^-$ may be repeated as in the case of dibasic quaternary salts having two pentavalent Group VA ions substituted in the manner described.

The preferred onium salts for use in the invention have the formula

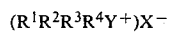
$$(R^1R^2R^3R^4Y^+)X^-$$

wherein Y is N or P, and $R^1$–$R^4$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be less preferentially less soluble in the less polar of the two distinct liquid phases. Any of the salts disclosed in U.S. Pat. No. 3,992,432 will be found effective, but most preferred are those in which the total number of carbon atoms in $R^1$, $R^2$, $R^3$, and $R^4$ cumulatively range from about 13 to about 57, and preferably range from about 16 to about 30. Most preferred onium salts have Y=N, and hydrocarbon radicals where $R^1$ is $CH_3$, and $R^2$, $R^3$, and $R^4$ are each selected from the group consisting of n-$C_4H_5$; n-$C_5H_{11}$; mixed $C_5H_{11}$; n-$C_6H_{13}$; mixed $C_6H_{13}$; $C_6H_5$; $C_6H_5CH_2$; n-$C_8H_{17}$; n-$C_{12}H_{25}$; n-$C_{18}H_{37}$; mixed $C_8$–$C_{10}$ alkyl; and the like. However, $R^1$ may also be selected from $C_2H_5$, n-$C_3H_7$ and n-$C_4H_9$.

Various counterions may be used, including $Cl^-$, $Br^-$, $I^-$, $NO_3^-$, $SO_4^-$, $HSO_4^-$ and $CH_2CO_2^-$. Most preferred are $I^-$, $Br^-$ and $Cl^-$.

The organic solvent may be any solvent in which the reactants are soluble and include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride and the like. Most preferred solvents are hydrochloromethylenes.

The presence of a haloform, such as chloroform, iodoform or bromoform appears to take part in the reaction as a necessary reagent, but also presumably as a catalyst, though the precise mechanism or the manner in which the haloform affects the reaction, is not understood. This hypothesis that a haloform is essential is based upon the fact that, when another solvent is substituted for the haloform, the reaction does not proceed without at least a trace of the haloform. The amount of haloform used does not appear to be critical, and only a minor amount by volume, as compared with the volume of organic solvent used, suffices. Preferred haloforms are chloroform and bromoform. It is essential that at least a stoichiometric amount of haloform be used if no amine is to be left unreacted. Though a small amount of unreacted amine is not deleterious, it is desirable to employ a slight excess over stoichiometric of the haloform to avoid unreacted amine. Though an excess, up to about a 50% excess over stoichiometric provides acceptable results, more than 50% over stoichiometric is to be avoided because of the formation of undesirable side products. A preferred amount of haloform is in excess of 20 percent by weight of the reaction mass, and chloroform is most preferred.

Though the amount of phase transfer catalyst used is not critical, its catalytic function appears to be unique in this "soft ion" catalyzed reaction. In general, it is sufficient to use no more onium salt catalyst than about 2 percent by weight of the reaction mass, and it is preferred to use in the range from about 0.1 to about 1 percent by weight.

The mono-ketone is preferably saturated and may be cyclic or acyclic. Useful ketones are those which cyclize forming a fixed two-carbon bridge between the $N^1$ and $N^4$ atoms of the diaza ring. Preferred monoketones are cycloalkanones, dialkylketones and aralkylketones.

The monoaldehyde is preferably saturated and may be cyclic or acyclic. Useful monoaldehydes are those which cyclize forming a fixed two-carbon bridge between the $N^1$ and $N^4$ atoms of the diaza ring. Preferred monoaldehydes are cycloaldehydes, dialkylaldehydes and aralkylaldehydes.

It will presently be recognized from the examples herein, that polyketones and polyaldehydes, for example diketones and dialdehydes, will yield bis compounds.

The preferred alkali is an aqueous alkali metal hydroxide solution such as aqueous sodium hydroxide, or potassium hydroxide, preferably in the range from about 20 percent to about 70 percent solutions. If the alkali metal hydroxide is used in solid form, it is preferably in finely divided powder form typically less than 80 U.S. Standard mesh in size. The amount used is not critical but at least a trace amount appears to be essential for the progress of the desired reaction. It is preferred to use sufficient aqueous alkali solution to form a visually distinct aqueous phase in the presence of the organic solvent phase. In general, the amount of aqueous alkali used is preferably at least 5 percent by weight of the reaction mass. There is no advantage to using more aqueous alkali than about 75 percent by weight of the reaction mass.

In general, this soft ion catalytic synthesis will provide at least one more-desirable isomer having substituents on both $N^4$-adjacent C atoms, and at least one less-desirable isomer having an $N^4$-adjacent C atom which is unsubstituted. It will also usually provide a solid reaction product of 2-keto-1,4-diazacycloalkane with substituents both at the 5-position (that is, the $N^4$-adjacent C atom of the variable length bridge), and also the $N^1$-adjacent C atom of the variable length bridge. In addition, where an amine moiety has an alkyl (say) substituent either the $N^1$ or $N^4$ atom, or both, may be alkyl substituted. Thus, starting with N-propyl-2-methyl-1,2-proppanediamine, the synthesis yields both $N^1$-propyl-3,3,5,5-tetramethyl-2-piperazinone and $N^4$-propyl-3,3,6,6-tetramethyl-2-piperazinone. On occasion, this synthesis will provide the more-desirable isomer substantially exclusively.

The following examples serve to illustrate the invention. Where not otherwise stated, parts are given as parts by weight and the temperatures in degrees centigrade.

EXAMPLE 1

Preparation of $N^1$-propyl-3,3,5,5-tetramethyl-2-piperazinone (I) and $N^4$-propyl-3,3,6,6-tetramethyl-2-piperazinone (II):

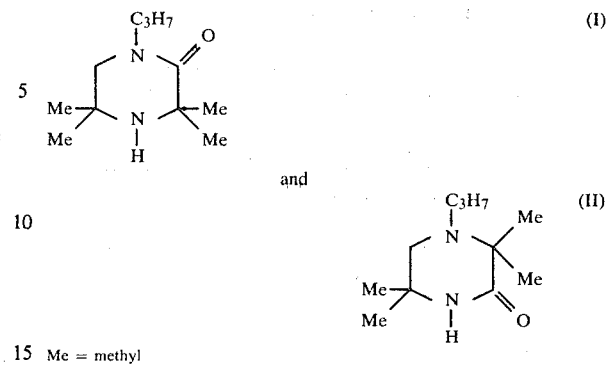

Me = methyl

A. 6.51 g N-propyl-2-methyl-1,2-propanediamine and 50 ml methylene chloride are placed in a 250 ml flask. 5.8 g acetone and 7.2 g chloroform are added to the flask, followed by 0.5 g BTAC. While stirring in an ice-bath, 20 ml conc NaOH (50% by wt) was added dropwise over about 0.5 hr. Water is added after the reaction has proceeded for at least a couple of hours, and all solids go into solution. Two distinct liquid phases are formed, and the layers are separated. The aqueous layer is extracted several times with 40 ml methylene chloride. The combined methylene chloride solutions are washed several times with $H_2O$, dried and concentrated. 8.6 g of a light yellow oil are obtained which is identified as (I) and (II) in a 7:3 ratio. The oil is distilled at 125°–7° C./8 mm and a colorless oil mixture of the compounds (I) and (II) is obtained. The foregoing structure of the compounds is supported by IR, NMR, GC and mass spectrometer data.

B. In a manner analogous to that described hereinabove for example 1A, a synthesis is now carried out with a soft ion catalyst added to the reactants. To the contents of the flask is added 0.1 equivalents (about 0.265 g) of sodium cyanide, the reactants stirred, and the conc. NaOH is then added dropwise. The isomers of the substituted 2-keto-piperazine formed are recovered, and separated. This soft ion synthesis is repeated with all condition remaining the same, except that other catalysts are also used. In particular, additional examples of the use of NaCN are provided in which the amount of NaCN is increased to 0.2 and 0.3 equivalents of the 1,2-diamine. The directive effect of the cyanide soft ion is set forth in Table I hereinbelow:

TABLE 1

| Soft ion catalyst | Amount used (equivalents) | Ratio of isomer with substituents on $N^4$-adjacent C atoms : isomers with an unsubstituted $N^4$-adjacent C atom |
|---|---|---|
| NaCN | 0 | 7 : 3 |
| NaCN | 0.1 | 9 : 1 |
| NaCN | 0.2 | 9.6 : 0.4 |
| NaCN | 0.3 | 9.8 : 0.2 |
| $(CH_3)_2C(OH)CN$ | 0.2 | 9.2 : 0.8 |
| NaI | 0.1 | 9.8 : 0.2 |

C. In a manner analogous to that described hereinabove for example 1B, syntheses are now carried out with lesser amounts of phase transfer catalyst (0.02 equivalents) and soft ion catalyst (0.06 equivalents) added to the reactants. The directive effect of the soft ion is set forth in Table II hereinbelow:

TABLE 2

| Soft ion catalyst | Amount used (equivalents) | Ratio of isomer with substituents on $N^4$-adjacent C atoms : isomers with an unsubstituted $N^4$-adjacent C atom |
|---|---|---|
| NaCN | 0 | 7 : 3 |
| NaCN | 0.06 | 9.4 : 0.6 |
| NaI | 0.06 | 9.9 : 0.1 |

EXAMPLE 2

Preparation of $N^1$-isopropyl-3,3-pentamethylene-5,5-dimethyl-2-piperazinone having the following structure:

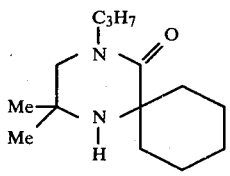

In a manner analogous to that described hereinabove in example 1A, et seq, starting with N-isopropyl-2-amino-2-methyl-1,2-propanediamine, cyclohexanone, chloroform and a phase transfer catalyst (BTAC), 0.3 equivalents of NaCN are added to the mixture at ice-bath temperature of about 0° C., and conc aqueous NaOH (50%) is added dropwise. The above-identified isomer with substituents on both $N^4$-adjacent C atoms of the diaza ring is formed to the substantial exclusion of other isomers.

EXAMPLE 3

Preparation of 1,2-ethane-bis-[1-(3,3,5,5,7-pentamethyl-1,4-diazacycloheptan-2-one)] having the following structure:

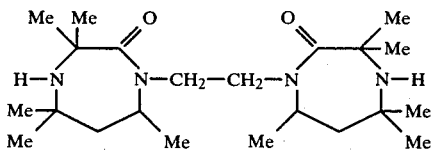

In a manner analogous to that described in example 1A hereinabove, starting with 1,2-ethane-bis-$N^1$[2-methyl-1,2-propanediamine], acetone, chloroform and a phase transfer catalyst (tributyl hexadecyl phosphonium bromide), about 0.3 equivalents of NaCN are added to the reactants, and then conc NaOH is dripped in as before. The bis compound having the aboveidentified structure is formed in a ratio of greater than 9.8:1; that is, more than 98 percent of the substituted bis compounds have the structure illustrated above. By comparison, in the absence of the NaCN soft ion catalyst, the ratio of the isomer with substituents on both $N^4$-adjacent C atoms:isomers with an unsubstituted $N^4$-adjacent C atom is about 8:2.

In a manner analogous to that described hereinabove, a substantial improvement is noted in the ratio of more-desirable isomer to less-desirable isomers when other soft ion catalysts are used. Among these catalysts are cyclohexanone cyanohydrin, sodium iodide, potassium iodide, calcium cyanide, calcium iodide, ammonium cyanide and ammonium iodide.

I claim:

1. A method for preparing a polysubstituted 2-keto-1,4-diazacycloalkane compound comprising reacting in liquid phase (A) an acyclic 1,2-diamine with (B) a compound having a carbonyl bond selected from the group consisting of monoketones and monoaldehydes, in the presence of (i) a soft ion selected from the group consisting of cyanide, iodide and thiocyanate, (ii) a haloform, (iii) alkali, and (iv) a phase transfer catalyst selected from the group consisting of tertiary and quaternary compounds of Group VA and Group VIA elements, and salts thereof, said soft ion together with said phase transfer catalyst being present in an amount sufficient to form said polysubstituted 2-keto-1,4-diazacycloalkane; forming said polysubstituted 2-keto-1,4-diazacycloalkane compound; and, recovering said polysubstituted compound.

2. The method of claim 1 wherein said acyclic 1,2-diamine is an alkyl diamine; said soft ion catalyst is selected from the group consisting of ketone cyanohydrins, inorganic cyanides, inorganic iodides and inorganic thiocyanates; said monoketone is selected from a cyclic ketone and an acyclic ketone; said haloform is selected from chloroform and bromoform; and, said alkali is an aqueous alkali metal hydroxide.

3. The method of claim 2 wherein said inorganic cyanides are selected from the group consisting of ammonium cyanide, alkali metal cyanides and alkaline earth metal cyanides; and, said inorganic iodides are selected from the group consisting of ammonium iodide, alkali metal iodides and alkaline earth metal iodides.

4. The method of claim 3 wherein said liquid phase is maintained at a temperature in the range from about $-20°$ C. to about room temperature.

5. The method of claim 4 wherein said acyclic 1,2-diamine is N-propyl-2-methyl-1,2-propanediamine; said compound having a carbonyl bond is selected from the group consisting of acetone and cyclohexanone; and, said haloform is selected from the group consisting of chloroform, bromoform and iodoform.

6. The method of claim 1 wherein said polysubstituted compound formed includes at least one less-desirable isomer having an $N^4$-adjacent C atom which is not substituted, and at least one more-desirable isomer having substituents on both $N^4$-adjacent C atoms, the ratio of said more desirable isomer formed to said less desirable isomer being at least 5:1.

7. The method of claim 6 wherein said soft ion is selected from the group consisting of cyanide and iodide.

8. The method of claim 6 wherein said soft ion is thiocyanate.

* * * * *